US007439383B2

(12) United States Patent
Brown

(10) Patent No.: US 7,439,383 B2
(45) Date of Patent: Oct. 21, 2008

(54) SODIUM CHANNEL BLOCKERS

(75) Inventor: Milton L. Brown, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 468 days.

(21) Appl. No.: 10/511,666

(22) PCT Filed: Apr. 18, 2003

(86) PCT No.: PCT/US03/12162

§ 371 (c)(1), (2), (4) Date: Oct. 18, 2004

(87) PCT Pub. No.: WO03/088915

PCT Pub. Date: Oct. 30, 2003

(65) Prior Publication Data

US 2005/0228033 A1 Oct. 13, 2005

Related U.S. Application Data

(60) Provisional application No. 60/373,784, filed on Apr. 19, 2002, provisional application No. 60/373,440, filed on Apr. 18, 2002.

(51) Int. Cl.

| | |
|---|---|
| ***C07C 63/00*** | (2006.01) |
| ***C07C 55/28*** | (2006.01) |
| ***C07C 233/00*** | (2006.01) |
| ***C07C 229/00*** | (2006.01) |

(52) U.S. Cl. .......................... 560/39; 560/41; 562/405; 562/433; 562/489; 564/123

(58) Field of Classification Search ................. 564/123; 560/39, 41; 562/405, 433, 489

See application file for complete search history.

(56) References Cited

U.S. PATENT DOCUMENTS

| | | | |
|---|---|---|---|
| 2,366,221 | A | 1/1945 | Spurlock |
| 2,526,232 | A | 10/1950 | Henze |
| 4,258,054 | A | 3/1981 | Sarges |
| 5,389,614 | A | 2/1995 | König et al. |
| 5,463,125 | A | 10/1995 | Sandoval et al. |
| 2002/0156016 | A1 | 10/2002 | Minuk |

FOREIGN PATENT DOCUMENTS

| | | | |
|---|---|---|---|
| EP | 0006407 | A1 | 1/1980 |
| EP | 0076957 | A1 | 4/1983 |
| EP | 0115133 | A1 | 8/1984 |
| EP | 0552631 | A1 | 7/1993 |

(Continued)

OTHER PUBLICATIONS

Grunewald et al , Tetrahedron Letters , 1980, 21 (13), p. 1219-1220 (a copy of abstract page ).*

(Continued)

*Primary Examiner*—Taylor Victor Oh
(74) *Attorney, Agent, or Firm*—Rodney L. Sparks

(57) ABSTRACT

The present invention is directed to novel phenytoin derivative compounds and the use of such compounds as sodium channel blockers. Such compositions have utility as anticancer agents and can be used to limit or prevent PCa growth and/or metastasis.

3 Claims, 1 Drawing Sheet

FOREIGN PATENT DOCUMENTS

| | | | |
|---|---|---|---|
| GB | 980250 | | 1/1965 |
| GB | 1566171 | | 4/1980 |
| SU | 447401 | | 10/1974 |
| WO | WO 99/41229 | A1 | 8/1999 |
| WO | WO 01/45704 | A1 | 6/2001 |
| WO | WO 02/083133 | A1 | 10/2002 |

OTHER PUBLICATIONS

Desphande, R.N. et al., (1970), "Synthesis of Hydantoins of Pharmacological Interest," Indian Journal of Chemistry, Section B: Organic, Incl. Medicinal, Publications & Informatioins Directorate, New Delhi, IN, vol. 8, No. 11, pp. 1043-1044.

Galvez, E. et al., (1983), "Synthesis and Structural Studey of Cyclopentane, Indene and Flourene Spiro-derivatives," Journal of Heterocyclic Chemistry, Heterocorporation. Provo, US, vol. 20, No. 1, pp. 13-16.

Sarges, R. et al., (1987), "Spiro Hydantoin Aldose Redutase Inhibitors," Journal of Medicinal Chemistry, vol. 31, No. 1, pp. 230-242.

Dupriest. M.T. et al., (1991), "Spiro[fluoreneisothiazolidin]one Dioxides: New Aldose Redutase and L-Hexonate dehydrogenase Inhibitors," Journal of Medicinal Chemistry, vol. 34, No. 11, pp. 3229-3234.

Abdul, M. et al., (2001), "Inhibition by Anticonvulsants of Prostate-specifice Antigen and Interleukin-6 Secretion by Human Prostate Cancer Cells," Anticancer Research, vol. 21, pp. 2045-2048.

Meza-Toledo, S.E. et al., (1995), "Stereoselective Anticonvulsant Activity of the Enantiomers of (.+-.)-2-Hydroxy-2-phenylbutyramide," Arzneimittel Forschung. Drug Research, vol. 45, pp. 756-759.

Meza-Toledo, S.E. et al., (1990), "A New Homologous Series of Anticonvulsants: Phenyl Alcohol Amides," Arzneimittel Forschung. Drug Research, vol. 40, pp. 1289-1291.

Wilimowski, M. et al., (1970), "Pharmacologic Properties of Derivatives of 3-Phenyl-3-Hydroxyglutaric Acid," Archivum Immunologiae et Therapiae Experimentalis, vol. 18, pp. 270-279.

Barrio, J. et al., (1971), "5-Cyclohexylmethyl-5-arylhydantoins," Journal of Medicinal Chemistry, vol. 14, No. 9, p. 898.

Brown, M.L. et al., (1999), "Comparative Molecular Field Analysis of Hydantoin Binding to the Neuronal Voltage-Dependent Sodium Channel," J. Med. Chem., vol. 42, pp. 1537-1545.

Knabe, J. et al., (1997), "Razemate und Enantiomere basisch substituierter 5-Phenylhydantoine, Synthese und antiarrhythmische Wirkung, Racemates and enantiomers of basic substituted 5-phenylhydantoins, synthesis and antiarrhythmic activity," Pharmazie, Die, Gopvi Verlag, Eschborn, De, vol. 52, pp. 912-919.

Casagrande, C. et al., (1974), "Synthesis and antiarrhythmic activity of 5,5-disubstituted-3-aminoalkylhydantoins and some heterocyclic and noncyclid analogues," Farmaco, Edizione Scientifica, Societa Chemica Italiana, Pavia IT, vol. 29, No. 10, pp. 757-785.

Brouillette, W.J. et al., (1990), "Sodium channel binding and anticonvulsant activities of hydantoins containing conformationally constrained 5-phenyl substituents," J. of Pharmaceutical Sciences, Am. Pharmaceutical Assoc. Washington, US, vol. 79, No. 10, pp. 871-874.

Kadam, A.N. et al., (1978), "Synthesis of gamma-(5-arylhydantoin-5)-butyric acids," J. of the Indian Chemical Society, Calcutta, IN, vol. 51, No. 1, pp. 107-108.

* cited by examiner

SODIUM CHANNEL BLOCKERS

RELATED APPLICATION

This application is a national stage filing of International Application No. PCT/US03/012162, filed on Apr. 18, 2003, which claims benefit under 35 USC § 119(e) to U.S. Provisional Application Ser. Nos. 60/373,440, filed Apr. 18, 2002, and 60/373,784, filed Apr. 19, 2002 the entire disclosures of which are incorporated herein.

FIELD OF THE INVENTION

The present invention is directed to novel compounds and the use of such compounds as sodium channel blockers. Such compositions have utility in treating diseases associated with inappropriate sodium channel activity, and include the use of these compounds as anti-cancer agents.

BACKGROUND OF THE INVENTION

The capacity of a cell to alter its morphology and migrate is inherent to cancer cell metastasis. Although the precise biological mechanisms shaping cellular morphology during metastasis have not been elucidated, it is known that such changes involve cell-matrix interactions and cytoskeletal elements. The involvement of Na+ channels in shaping cellular morphology has been described for neurons (Mattei et al., Journal of Neuroscience Research, 55(6):666-73, 1999). As of yet, the intracellular mechanisms through which Na+ channel activity regulate cancer cellular morphology are unclear, although ion channels have been implicated in several types of cellular behavior that could be related to the different stages of metastasis. These include proliferation, migration, and adhesion/interaction with the cellular matrix.

Voltage-gated ion channels, classically associated with impulse conduction in excitable tissues, are also found in a variety of epithelial cell types where their function is not well known. Nine mammalian sodium channel genes have been identified and found to be expressed and functional. These genes are greater than 50% identical in amino acid sequence in the transmembrane and extracellular domains. Recently, several types of voltage-gated ion channels have been discovered in rat and human prostate cancer cells. Several independent studies have also linked a prostate voltage gated sodium (Na+) channel α-subunit with the invasiveness of human prostate cell lines including LNCaP and PC-3 (see Diss, et al., The Prostate, 48:165-178, 2001 and Smith et al., FEBS Letters, 423:19-24, 1998.). Further, electrophysiological studies using a whole-ell patch clamp indicated that the identified prostate cell sodium channel is sensitive to tetrodotoxin (TTX) at 600 nM, identifying the channel as voltage dependent TTX sensitive Na+ channel protein.

Comparisons between rodent and human prostate cancer cell lines led to the conclusion that the level of Na+ channel expression is associated positively with the invasiveness of prostate cancer cells in vitro. Encouragingly, both protein and functional studies strongly support sodium channel blockade as a viable mechanism for PCa cell inhibition. Recently, the effect of four anticonvulsants on the secretion of prostate-specific antigen (PSA) and interleukin-6 (IL-6) by human prostate cancer cell lines (LNCaP, DU-145 and PC-3) was measured using ELISA's specific for each protein. The results demonstrated that both phenytoin and carbamazepine, which inactivate voltage-gated sodium channels (NVSC), inhibit the secretion of PSA by LNCaP and IL-6, DU-145 and PC-3 cell lines (Abdul, M. and Hoosein, N., Anticancer Research, 21(3B):2045-8, 2001 May-June). Additionally, the authors demonstrate a reduced capacity to form colonies in Matrigel upon treatment with phenytoin. These data indicate further that sodium channel blockade is a strong candidate for effective treatment of PCa.

Experiments using tritiated batrachotoxin (BTX) have revealed an allosteric relationship between BTX and the phenytoin binding site in brain tissue. This relationship led applicant to investigate the neuronal hydantoin receptor in the brain for conformation and lipophilic properties. Since there was little structural data about the phenytoin-binding site on the NVSC, a defined series of compounds was designed, synthesized and evaluated to identify novel Na+ channel blocking agents. Such compounds have utility in treating diseases associated with hyper sodium channel activity, including treating epilepsy, pain, bipolar disease, depression Amytrophic lateral sclerosis (ALS) and neoplastic disease such as androgen-sensitive and androgen-independent prostate cancer.

Prostate neoplasia is the most common cause of cancer in men and the second leading cause of cancer death among men in the U.S. Approximately 189,000 men will be diagnosed with prostate cancer and approximately 30,000 will die from this disease in 2002. Human prostate cancer cells express a voltage gated sodium channel, a 260 Kd transmembrane protein that is similar to neuronal subtypes. Whole cell patch clamping experiments indicate that the prostate voltage sodium channel (PVSC) also functions similarly to neuronal subtypes. Significantly, Na+ channel expression in prostate cancer cells has been correlated positively to invasiveness in the highly metastatic cell line MAT-LyLu (rat). PVSC has been found to be sensitive to Tetrodotoxin (TTX) and it has been reported that TTX inhibits the invasiveness of PC-3 cells (human) by 31% (P=0.02) Laniado, et al. American Journal of Pathology, 150(4): 1213-21, 1997. Furthermore, TTX (6 mM) produces alterations in prostate cancer cell morphology, including a decrease in cell process length, field diameter; increases in cell body diameter and process thickness. S. P. Fraser, Y. Ding, A. Liu, C. S. Foster M. B. A. Djamgoz. Cell Tissue Research. 295: 505-512, 1999 and Grimes J A. Djamgoz M B. Journal of Cellular Physiology. 175(1):50-8, 1998. Therefore, PVSC serves as an effective target for potential prostate cancer therapeutics, thus presenting a need for new inhibitors of this sodium channel.

SUMMARY OF THE INVENTION

The present invention is directed to the design and synthesis of novel voltage-gated sodium channel (VGSC) and prostate voltage sodium channel (PVSC) inhibitors. Compositions comprising such inhibitors have utility in treating diseases characterized by overabundant or hyperactive VGSC/PVSC's. In one embodiment a sodium channel binder/blocker that selectively targets overabundant or hyperactive VGSC's in the prostate is used to limit or prevent PCa growth and/or metastasis.

DETAILED DESCRIPTION OF THE INVENTION

Definitions

Figure 1:
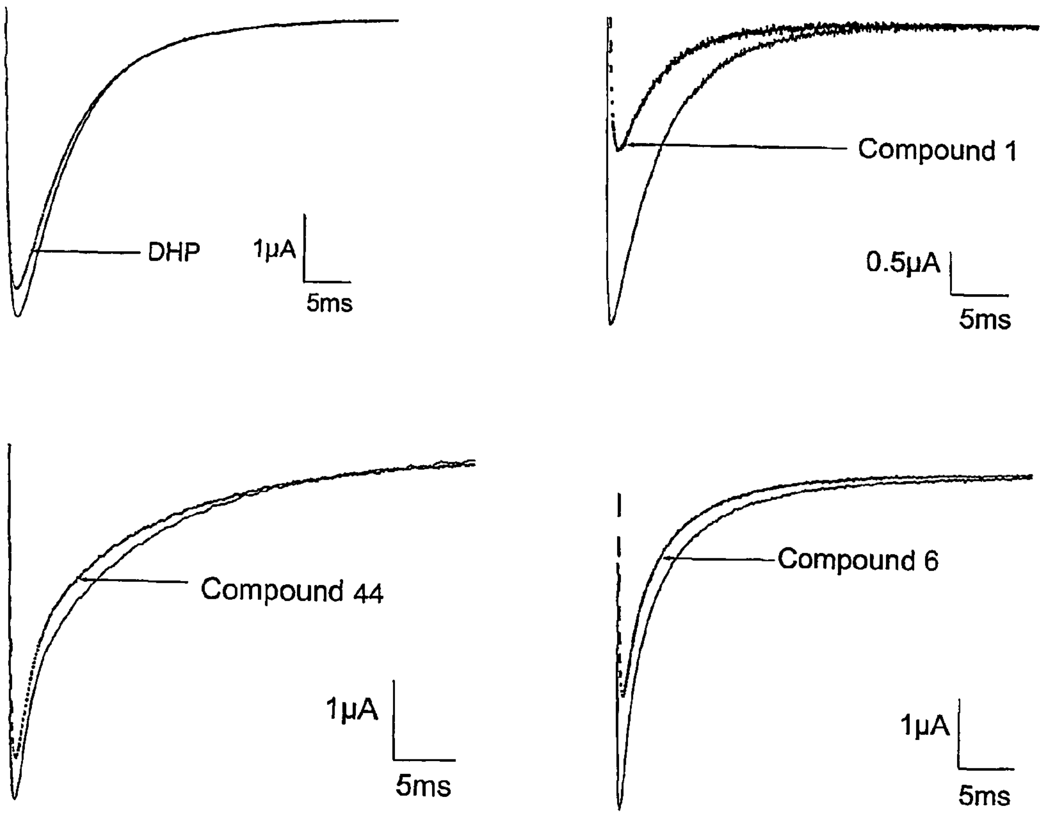
FIG. 1: Effects of phenytoin DIP) and analogues 1, 5 and 44 on the rNav1.2. Currents were elicited by a step depolarisation from a holding potential of −100 mV to +10 mV for 50 msec at 15 sec intervals. In each example a control trace is superimposed with one recorded at maximum drug affect. All compounds were tested at 100 μM concentration.

In describing and claiming the invention, the following terminology will be used in accordance with the definitions set forth below.

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, an "effective amount" means an amount sufficient to produce a selected effect. For example, an effective amount of a sodium channel blocker is an amount of the blocker sufficient to produce a detectable inhibition of sodium channel activity.

The general chemical terms used in the description of the compounds of the present invention have their usual meanings. For example, the term "alkyl" by itself or as part of another substituent means a straight or branched aliphatic chain having the stated number of carbon atoms.

The term "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, refers to a branched or linear alkyl group having from one to the specified number of carbon atoms. Typically $C_1$-$C_6$ alkyl groups include, but are not limited to, methyl, ethyl, n-propyl, iso-propyl, butyl, iso-butyl, sec-butyl, tert-butyl, pentyl, hexyl and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

As used herein, the term "optionally substituted" refers to zero to four substituents, wherein the substituents are each independently selected. More preferably, the term refers to zero to three independently selected substituents.

As used herein the term "aryl" refers to a mono- or bicyclic carbocyclic ring system having one or two aromatic rings including, but not limited to, phenyl, naphthyl, tetrahydronaphthyl, indanyl, indenyl, and the like. Aryl groups (including bicyclic aryl groups) can be unsubstituted or substituted with one, two or three substituents independently selected from lower alkyl, haloalkyl, alkoxy, amino, alkylamino, dialkylamino, hydroxy, halo, and nitro. The term (alkyl)aryl refers to any aryl group which is attached to the parent moiety via the alkyl group.

The term "$C_3$-$C_n$ cycloalkyl" wherein n=4-8, represents cyclopropyl, cyclobutyl, cyclopentyl, cyclohexyl, cycloheptyl, and cyclooctyl.

The term "heterocyclic group" refers to a $C_3$-$C_8$ cycloalkyl group containing from one to three heteroatoms wherein the heteroatoms are selected from the group consisting of oxygen, sulfur, and nitrogen.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "lower alkyl" as used herein refers to branched or straight chain alkyl groups comprising one to eight carbon atoms, including methyl, ethyl, propyl, isopropyl, n-butyl, t-butyl, neopentyl and the like.

The term, "parenteral" means not through the alimentary canal but by some other route such as subcutaneous, intramuscular, intraspinal, or intravenous.

As used herein, the term "treating" includes alleviating the symptoms associated with a specific disorder or condition and/or preventing or eliminating said symptoms.

As used herein the term "anti-tumor agent" relates to agents known in the art that have been demonstrated to have utility for treating neoplastic disease. For example, antitumor agents include, but are not limited to, antibodies, toxins, chemotherapeutics, enzymes, cytokines, radionuclides, photodynamic agents, and angiogenesis inhibitors. Toxins include ricin A chain, mutant Pseudomonas exotoxins, diphtheria toxoid, streptonigrin, boamycin, saporin, gelonin, and pokeweed antiviral protein. Chemotherapeutics include 5-fluorouracil (5-FU), daunorubicin, cisplatinum, bleomycin, melphalan, taxol, tamoxifen, mitomycin-C, and methotrexate. Radionuclides include radiometals. Photodynamic agents include porphyrins and their derivatives. Angiogenesis inhibitors are known in the art and include natural and synthetic biomolecules such as paclitaxel, O-(chloroacetyl-carbonyl) fumagillol ("TNP-470" or "AGM 1470"), thrombospondin-1, thrombospondin-2, angiostatin, human chondrocyte-derived inhibitor of angiogenesis ("hCHIAMP"), cartilage-derived angiogenic inhibitor, platelet factor-4, gro-beta, human interferon-inducible protein 10 ("IP10"), interleukin 12, Ro 318220, tricyclodecan-9-yl xanthate ("D609"), irsogladine, 8,9-dihydroxy-7-methyl-benzo[b]quinolizinium bromide ("GPA 1734"), medroxyprogesterone, a combination of heparin and cortisone, glucosidase inhibitors, genistein, thalidomide, diamino-antraquinone, herbimycin, ursolic acid, and oleanolic acid.

The novel VGSC blockers of the present invention contain one or more asymmetric centers in the molecule. In accordance with the present invention a structure that does not designate the stereochemistry is to be understood as embracing all the various optical isomers, as well as racemic mixtures thereof.

The Invention

The present invention relates to the discovery of novel sodium channel blockers and the use of those compounds to treat diseases associated with excessive voltage gated sodium channel activity. In accordance with the present invention a modulator of voltage gated sodium channels is provided wherein the modulator has the general structure:

I

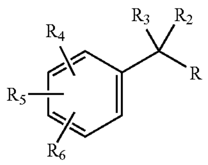

wherein R is selected from the group consisting of $C_1$-$C_{12}$ alkyl, $C_2$-$C_8$ alkenyl, $C_2$-$C_8$ alkynyl, —$(CH_2)_m$COOH, —$(CH_2)_m NH_2$, —$(CH_2)_m CONH_2$, —$(CH_2)_n C_3$-$C_6$ cycloalkyl, —$(CH_2)_p$(CHOH)$CONH_2$, —$(CH_2)_n$substituted aryl, —$(CH_2)_p NCH_3(CH_2)_p$ substituted aryl —$(CH_2)_n$aryl, and —$(CH_2)_n$ substituted heterocyclic, wherein m is an integer ranging from 3-8, n is an integer ranging from 0-4 and p is an integer ranging from 1-4. $R_2$ is selected from the group consisting of H, $C_1$-$C_8$ alkyl, —$(CH_2)_n$COOH, —$(CH_2)_n NH_2$, —$(CH_2)_n$ $NHCH_3$, and —$(CH_2)_n CONHR_{10}$, $R_3$ is selected from the group consisting of H, hydroxy, amino, ($C_1$-$C_4$) alkoxy, —$CH_2OH$ and —$CONH_2$, or $R_2$ and $R_3$ taken together with the atoms to which they are attached form an optionally substituted aryl or an optionally substituted heterocyclic ring, $R_4$ and $R_5$ are independently selected from the group consisting of H, halo, $C_1$-$C_4$ alkyl, $C_2$-$C_4$ alkenyl, $C_2$-$C_4$ alkynyl, —$COR_{11}$ and ($C_1$-$C_4$) alkoxy, and $R_6$ is selected from the group consisting of H, halo, $C_1$-$C_8$ alkyl, amino, hydroxy, $C_1$-$C_8$ alkoxy,

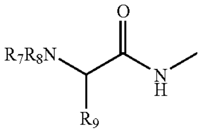

and

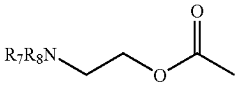

, wherein $R_7$ and $R_8$ are independently selected from the group consisting of H, $C_1$-$C_4$ alkyl, $C_2$-$C_4$ alkenyl and $C_2$-$C_4$ alkynyl, and $R_9$ is H, or $R_8$ and $R_9$ taken together with the atoms to which they are attached form an optionally substituted heterocyclic ring, $R_{10}$ is selected from the group consisting of H and $C_1$-$C_4$ alkyl, and $R_{11}$ is selected from the group consisting of H, $C_1$-$C_4$ alkyl, $NH_2$ and OH, with the proviso that when $R_4$, $R_5$ and $R_6$ are each H, and $R_2$ and $R_3$ taken together form a heterocyclic ring, R is not —$(CH_2)_n$aryl.

In one embodiment the compound has the general structure of Formula I, wherein $R_2$ and $R_3$ taken together with the atoms to which they, are attached form a heterocyclic ring having the structure:

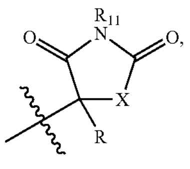

wherein X is selected from the group consisting of —$CHR_{12}$—, —O— and —$NR_{12}$—, wherein $R_{11}$ and $R_{12}$ are independently selected from the group consisting of H, benzyl and $C_1$-$C_4$ alkyl, with the proviso that when X is —$NH_2$— and $R_{11}$ is H, R is not phenyl. In one preferred embodiment X is —$NR_{12}$—.

In one embodiment the compound has the general structure of Formula I, wherein R is selected from the group consisting of $C_1$-$C_{12}$ alkyl, $C_2$-$C_8$ alkenyl, $C_2$-$C_8$ alkynyl, $R_2$ and $R_3$ taken together with the atoms to which they are attached form a ring having the structure:

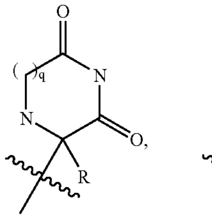

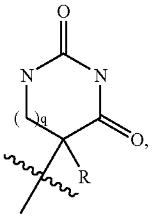

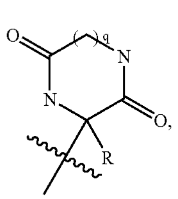

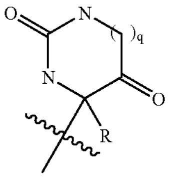

and

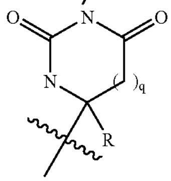

wherein q is an integer ranging from 1 to 2. In one preferred embodiment R is $C_1$-$C_{12}$ alkyl, q is 1 and $R_4$, $R_5$ and $R_6$ are independently selected from the group consisting of H and halo.

In accordance with one embodiment a sodium channel blockers is provided wherein the blocker has the general structure:

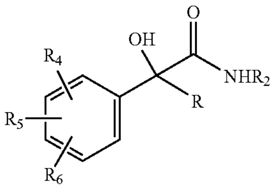

or

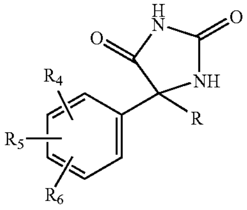

wherein R is selected from the group consisting of $C_1$-$C_{12}$ alkyl, $C_2$-$C_8$ alkenyl, $C_2$-$C_8$ alkynyl, —$(CH_2)_n C_3$-$C_6$ cycloalkyl,

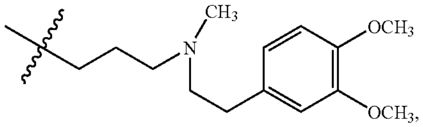

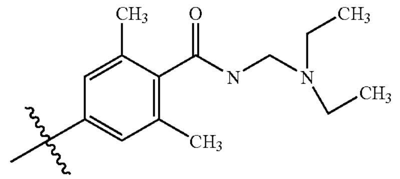

and

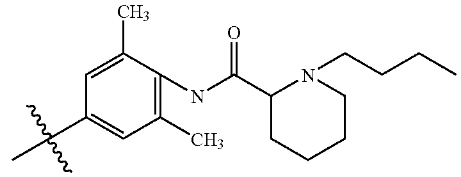

wherein n is an integer ranging from 0-4. $R_2$ is H or $C_1$-$C_4$ alkyl, $R_4$ and $R_5$ are independently selected from the group consisting of H, halo, $C_1$-$C_4$ alkyl, $C_2$-$C_4$ alkenyl, $C_2$-$C_4$ alkynyl, —$COR_{10}$ and ($C_1$-$C_4$) alkoxy, and $R_6$ is selected from the group consisting of H, halo, $C_1$-$C_8$ alkyl, amino, hydroxy, $C_1$-$C_8$ alkoxy and

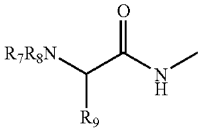 and 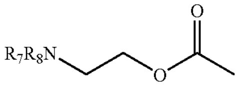 , wherein $R_7$ and $R_8$ are independently selected from the group consisting of H, $C_1$-$C_4$ alkyl, $C_2$-$C_4$ alkenyl and $C_2$-$C_4$ alkynyl, and $R_9$ is H, or $R_8$ and $R_9$ taken together with the atoms to which they are attached form an optionally substituted heterocyclic ring and $R_{10}$ is selected from the group consisting of H, $C_1$-$C_4$ alkyl, $NH_2$ and OH.

In one embodiment a compound that modulates sodium channel activity is provided wherein the compound is represented by the general structure

III

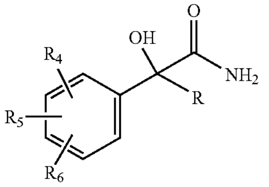 or

IV

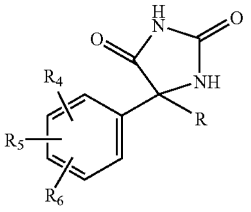

wherein R is selected from the group consisting of $C_3$-$C_{10}$ alkyl,

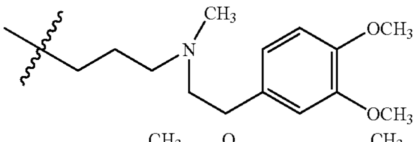 and

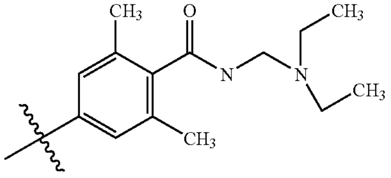

$R_4$ and $R_5$ are independently selected from the group consisting of H, halo, $C_1$-$C_4$ alkyl, and —$OCH_3$, and $R_6$ is selected from the group consisting of H,

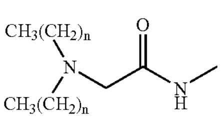 , 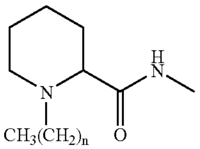 and

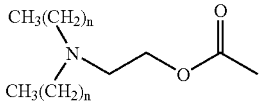

wherein n is an integer ranging from 0-4. In accordance with one embodiment the compound has the general structure of Formula III or IV wherein R is $C_3$-$C_9$ alkyl and $R_4$ and $R_5$ are independently H or methyl and $R_6$ is selected from the group consisting of

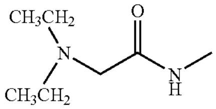 and 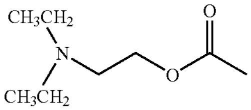

In accordance with one embodiment of the present invention a compound is provided that is represented by the general structure

III

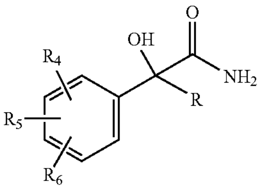 or

IV

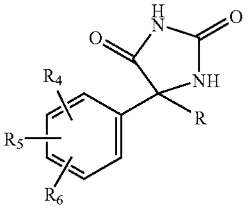

wherein R is selected from the group consisting of $C_3$-$C_9$ alky, $C_2$-$C_9$ alkenyl, and $C_2$-$C_9$ alkynyl, $R_4$ and $R_5$ are independently selected from the group consisting of H, halo, $C_1$-$C_4$ alkyl, $C_2$-$C_4$ alkenyl, $C_2$-$C_4$ alkynyl, and —$OCH_3$, and $R_6$ is selected from the group consisting of H, halo, $C_1$-$C_8$ alkyl, amino, hydroxy, and

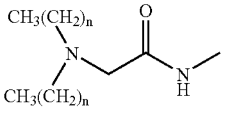 , 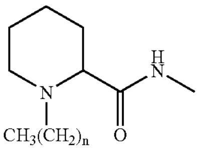 and

-continued

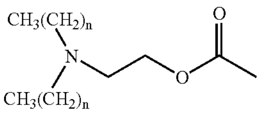

wherein n is an integer ranging from 0-4. In accordance with one embodiment the compound has the general structure of Formula III or IV wherein R is $C_3$-$C_{12}$ alkyl and $R_4$, $R_5$ and $R_6$ are independently selected from the group consisting of H and halo. In an alternative embodiment, the compound has the general structure of Formula III or IV wherein R is $C_3$-$C_{12}$ alkyl, $R_4$ and $R_5$ are independently H or $C_1$-$C_4$ alkyl and $R_6$ is selected from the group consisting of

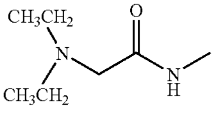

and

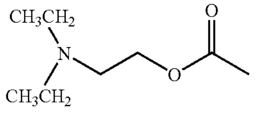

In another embodiment of the present invention a compound of the general formula III or IV is provided wherein R is

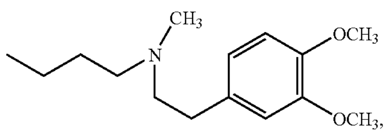

$R_4$ and $R_5$ are independently selected from the group consisting of H, halo, $C_1$-$C_4$ alkyl, and —$OCH_3$, and $R_6$ is H.

In another embodiment the sodium channel blocker of the present invention has the general structure

II

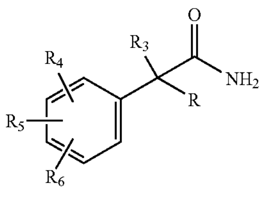

wherein R is selected from the group consisting of $C_1$-$C_{12}$ alkyl, $C_2$-$C_9$ alkenyl and $C_2$-$C_9$ alkynyl, $R_3$ is hydroxy, amino, ($C_1$-$C_4$) alkoxy, —$CH_2OH$ or —$CONH_2$, $R_4$ and $R_5$ are independently selected from the group consisting of H and halo, and $R_6$ is selected from the group consisting of H, halo and

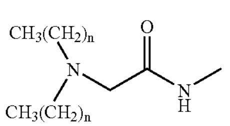

,

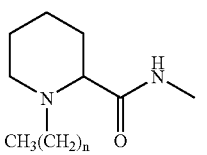

and

-continued

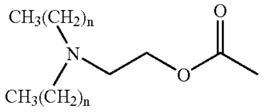

wherein n is an integer ranging from 0-4, and in one embodiment n is 1 or 2. In one preferred embodiment, a sodium channel blocker represented by formula II is provided wherein R is $C_1$-$C_{12}$ alkyl, $R_3$ is hydroxyl, $R_4$ is halo and $R_5$ and $R_6$ are halo or H, and in one preferred embodiment the halo substitutents are either F or Cl. In a further embodiment a compound of the general structure of Formula II is provided wherein R is $C_5$-$C_9$, $R_3$ is hydroxyl, $R_4$ and $R_5$ are both H and $R_6$ is halo, and more preferably F or Cl. In one preferred embodiment the present invention is directed to compounds of the general structure of Formula II wherein R is —$(CH_2)_6CH_3$, $R_3$ is hydroxyl, $R_4$ and $R_5$ are both H and $R_6$ is para-F or meta-Cl.

One aspect of the present invention is directed to the inhibition of voltage gated sodium channels as a novel method of targeting neoplastic cells and inhibiting metastasis. Several studies have identified the presence of sodium channel isotypes in prostate cancer cells. Sodium channel mRNA from two highly metastatic prostatic epithelial tumor cell lines MAT-Ly-Lu (rat) and PC-3 (human) was identified as the full-length skeletal muscle type 1 (SkM1). In situ hybridization data suggests that the level and pattern of rSkM1 mRNA expression were different in the Dunning cells of markedly different metastatic potential. Interestingly, the same type of mRNA was also detected in the weakly metastatic counterparts of AT-2 (rat) and LNCaP (human) PCa cells. Diss et. al. (The Prostate, 48:165-178, 2001), used semi-quantitative reverse transcription polymerase chain reaction (RT-PCR) to determine the expression profile of sodium channel mRNAs in several prostate cancer (PCa) cell lines. These results indicate that four different VGSC genes with 9 splice variants are expressed in LNCaP cells while PC-3 has 11 splice variants of the same mRNAs. Many of these splice variants encode the fetal form of the VGSC. It has recently been reported that prostate cancer cells express a voltage gated sodium channel (VGSC) and that the activity of this channel protein correlates with cellular invasiveness.

A study of VGSCs in the LNCaP and PC-3 human prostate cancer cell lines by Western blotting and flow cytometry reveal this channel to be a 260-kd protein representative of an alpha subunit (Komuro, et al., Science, 257: 806-809, 1992). Electrophysiological studies, using the whole-cell patch clamp technique demonstrate that the current elicited by this channel was inhibited by tetrodotoxin (TTX) at 600 nmol/L, thus identifying the subunit as a Na+ channel. Furthermore, it has been reported that the highly metastatic (rat) MAT-LyLu PCa cell line, derived from the Dunning model of rat prostate cancer, express a VGSC while the less metastatic (rat) AT-2 PCa cell line does not. Blockage of Na+ current with TTX significantly reduced the invasiveness of the MAT-LyLu cells in vitro, suggesting that the expressed channel has a functional role in metastasis. Moreover, the invasiveness of MAT-LyLu cells in vitro was inhibited by up to 50% with 6 μM TTX, a specific VGSC inhibitor. TTX exposure (incubation of MAT-LyLu for 24 h with 6 μM TTX) also altered several morphological features associated with an aggressive or highly motile phenotype, and more particularly, exposure to TTX decreased cell process length, field diameter, and increasing cell body diameter and process thickness.

The results obtained using TTX suggest that the Na+ channel may play a significant role in determining the morphological development of MAT-Ly-Lu cells in such a way as to enhance their metastatic potential. Further characterization of the current of these channels, using the whole-cell patch clamping, was conducted and the measured currents were compared to Na+ currents found in various other tissues. It was shown that the inward current of the Mat-Ly-Lu cells was abolished completely, but reversibly, in Na+-free solution. This confirms that Na+ was indeed the permeant ion. Similar data were obtained from human PCa cell lines. PC-3 cells treated with TTX had a 31% (P=0.02) reduction of invasiveness in vitro using Boyden chamber assays. The TTX mediated reduction in the invasiveness of PC-3 cells strongly suggests that ion channel modulators play an important functional role in human tumor invasion. However, TTX (which comes from puffer fish) is very toxic to live organisms and thus is not a suitable candidate for pharmaceutical formulations.

Recently, Abdul et. al., demonstrated that PCa specimens have higher levels of sodium channel expression compared to normal prostate (see Anticancer Research, 21(3B):2045-8, 2001). In addition, they also showed that a VGSC-opener (veratrine) increased proliferation, while VGSC-blockers (flunarizine and riluzole) caused dose dependent inhibition of PCa cell growth in the micromolar range. Taken together, these studies establish that PCa cell lines from both rat and human express VGSCs that are part of the tumorigenic behavior of these cell lines.

In accordance with one embodiment of the present invention a method is provided for treating a warm blooded vertebrate patient, including humans, afflicted by a neoplastic disease, such as prostate cancer. The method comprises the steps of administering to such a patient an effective amount of a composition comprising a sodium channel blocker represented by the general structure:

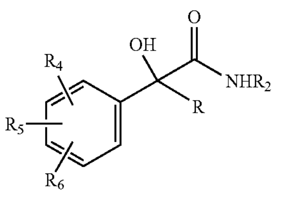

or

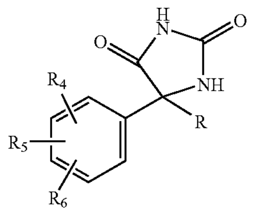

wherein R is selected from the group consisting of $C_1$-$C_{12}$ alkyl, $C_2$-$C_8$ alkenyl, $C_2$-$C_8$ alkynyl, —$(CH_2)_n C_3$-$C_6$ cycloalkyl,

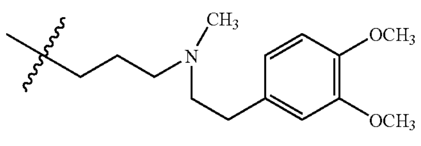

and

-continued

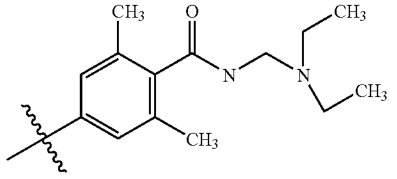

wherein n is an integer ranging from 0-4;

$R_2$ is selected from the group consisting of H, $C_1$-$C_8$ alkyl, —$(CH_2)_n$COOH, —$(CH_2)_n NH_2$, —$(CH_2)_n NHCH_3$, and —$(CH_2)_n CONH_2$;

$R_4$ and $R_5$ are independently selected from the group consisting of H, halo, $C_1$-$C_4$ alkyl, $C_2$-$C_4$ alkenyl, $C_2$-$C_4$ alkynyl, —$COR_{11}$ and ($C_1$-$C_4$) alkoxy; and $R_6$ is selected from the group consisting of H, halo,

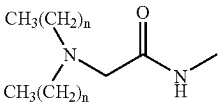

,

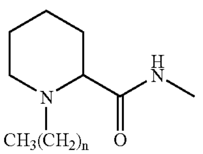

and

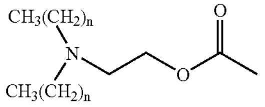

wherein $R_{11}$ is selected from the group consisting of H, $C_1$-$C_4$ alkyl, $NH_2$ and OH. In one preferred embodiment the patient is treated with a compound represented by the general structure of Formula III or IV wherein R is selected from the group consisting of $C_1$-$C_{12}$ alkyl, $R_2$ is H, $R_4$ and $R_5$ are independently selected from the group consisting of H, halo and $C_1$-$C_4$ alkyl and $R_6$ is selected from the group consisting of H, halo,

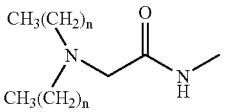

and

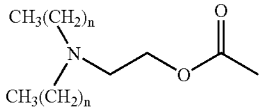

wherein n is 1 or 2. These sodium channel blocking compounds can be combined, or used in conjunction with, other known anti-tumor agents or therapies, such as chemotherapeutics or radiation treatments, to effectively treat cancer patients.

In accordance with one embodiment of the present invention a method for inhibiting voltage-gated sodium channel activity in a subject is provided, as a means of treating an illness associated with inappropriate sodium channel activity. The inappropriate activity will typically constitute channel hyperactivity or it may represent the expression of a voltage channel variant in a cell/tissue that normally does not express that channel. Existing sodium channel blockers have been used to treat a number of diseases, including epilepsy, bipolar disease, depression, pain, ALS, and arrhythmia. It is anticipated that the sodium channel blockers of the present invention will have utility as neuroprotective agents (including preventing secondary neuronal death after an initial injury) as well treating any of the disease states previously treated with sodium channel blockers.

In accordance with one embodiment a method of treating a disease state characterized by inappropriate sodium channel activity comprises the steps of administering a composition comprising a compound represented by the general structure:

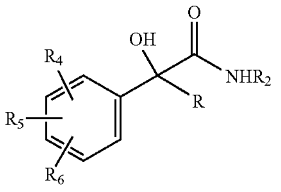
or
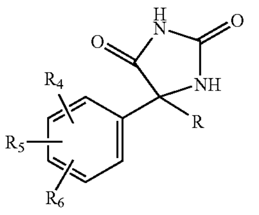

wherein R is selected from the group consisting of $C_1$-$C_{12}$ alkyl, $C_2$-$C_8$ alkenyl, $C_2$-$C_8$ alkynyl, —$(CH_2)_n C_3$-$C_6$ cycloalkyl,

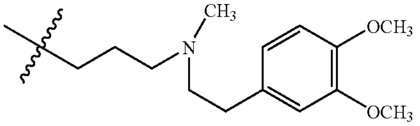
and
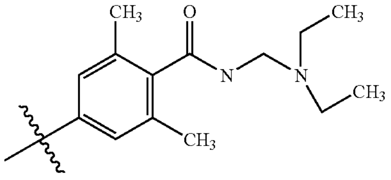

$R_2$ is selected from the group consisting of H, $C_1$-$C_8$ alkyl, —$(CH_2)_n$COOH, —$(CH_2)_n NH_2$, —$(CH_2)_n NHCH_3$, and —$(CH_2)_n CONH_2$;

$R_4$ and $R_5$ are independently selected from the group consisting of H, halo, $C_1$-$C_4$ alkyl, $C_2$-$C_4$ alkenyl, $C_2$-$C_4$ alkynyl, —$COR_{11}$ and ($C_1$-$C_4$) alkoxy; and $R_6$ is selected from the group consisting of H, halo,

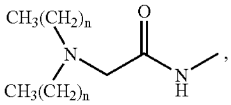
,
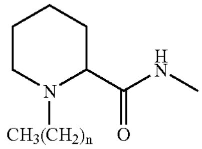
and
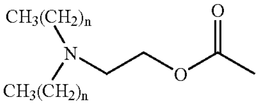

wherein n is an integer ranging from 0-4, and $R_{11}$ is selected from the group consisting of H, $C_1$-$C_4$ alkyl, $NH_2$ and OH.

As disclosed herein two classes of sodium channel blockers have been demonstrated as being effective inhibitors of prostate cancer cell proliferation. Both hydroxyamides of the general Formula III and hydantoins of the general Formula IV were shown to inhibit androgen dependent and independent cell lines in vitro. Tritiated thymidine uptake assays in PC-3 cells using hydantoin analogue 44 showed 55% inhibition of DNA synthesis at 40 μM (see Table 3 in Example 4). Further, these analogues demonstrated only marginal impact on cell viability after 24 hours treatment (Table 4 in Example 4). The sodium channel blockers of the present invention also demonstrated cell selective inhibition of growth in a long-term growth assay over several cell lines. In development of prostatic neoplasia, the time from tumor initiation and progression to invasive carcinoma often begins in men in the fourth and fifth decades of life and extends across many decades. Because of the protracted course of this disease the use of chemopreventive strategies or cytostatic strategies may be ideal in the treatment of prostate cancer.

In accordance with one embodiment of the present invention a method is provided for inhibiting the proliferation of neoplastic cells, and more particularly in one embodiment, prostate cancer cells. The method comprises contacting the cells with a compound represented by the general structure:

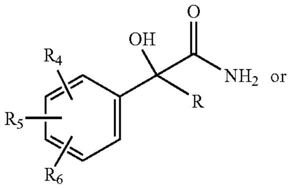
or
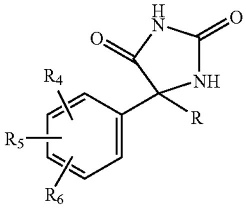

wherein R is selected from the group consisting of $C_1$-$C_{12}$ alkyl, $C_2$-$C_8$ alkenyl and $C_2$-$C_8$ alkynyl;

$R_4$ and $R_5$ are independently selected from the group consisting of H, halo, $C_1$-$C_4$ alkyl, —$COR_{11}$ and ($C_1$-$C_4$) alkoxy; and $R_6$ is selected from the group consisting of H, halo,

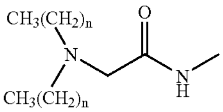
and
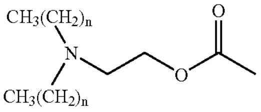

wherein $R_{11}$ is selected from the group consisting of H, $C_1$-$C_4$ alkyl, $NH_2$ and OH. In one embodiment R is selected from the group consisting of $C_1$-$C_{12}$ alkyl, $R_4$ and $R_5$ are independently selected from the group consisting of H, halo and $C_1$-$C_4$ alky, and $R_6$ is selected from the group consisting of H,

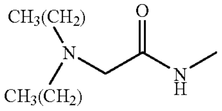
and
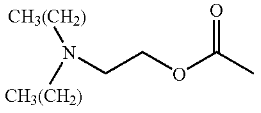

In another embodiment R is selected from the group consisting of $C_1$-$C_2$ alkyl, $C_2$-$C_8$ alkenyl, $C_2$-$C_8$ alkynyl, $R_4$ and $R_5$ are independently selected from the group consisting of H and halo, and $R_6$ is H. These compounds can be further combined with pharmaceutically acceptable carriers and other therapeutic compounds (such as anti-tumor agents) to provide therapeutic pharmaceutical compositions for treating neoplastic diseases, including breast, glioma and prostate cancers.

The sodium channel blocker compositions of the present invention can be administered either orally or parenterally. In one embodiment the composition is administered locally by injection or by an implantable time release device. When administered orally, the compounds can be administered as a liquid solution, powder, tablet, capsule or lozenge. The compounds can be used in combination with one or more conventional pharmaceutical additives or excipients used in the preparation of tablets, capsules, lozenges and other orally administrable forms. When administered parenterally, and more preferably by intravenous injection, the sodium channel blockers of the present invention can be admixed with saline solutions and/or conventional IV solutions.

One embodiment of the present invention is directed to pharmaceutical compositions comprising the compounds of the invention and a pharmaceutically acceptable carrier. The pharmaceutically acceptable carrier can be selected from among the group consisting of excipients, disintegrating agents, binders and lubricating agents. The amount of the pharmaceutical agent suitable for administration will be in accordance with standard clinical practice. The amount of the pharmaceutical agent suitable for administration will be in accordance with standard clinical practice. In addition the pharmaceutical compositions can be further combined with known anti-tumor agents and used in conjunction with known anti-tumor therapies.

EXAMPLE 1

Organic Synthesis of the Proposed Compounds.

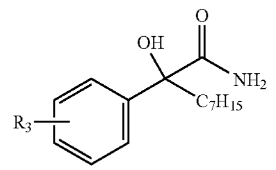

| Cmp | $R_3$ |
|---|---|
| 1 | 3-Cl |
| 2 | 4-Cl |
| 3 | 2-Cl |
| 4 | 4-OCH3 |
| 5 | H |
| 9 | 4-Fl |

Hydroxyamide compounds 1-5 were synthesized according to literature procedures and as outlined in Scheme I. In general, the corresponding nitrile was converted to the ketone by grignard addition followed by the conversion of the ketone to the TMS ether using TMSCN. The TMS ether was cleaved to the cyanohydrin with 1% HCl and the corresponding cyanohydrin hydrolyzed to the final product using concentrated HCl/HCl gas to generate the final compounds. Hydantoin analogues 44 and 66 were prepared by the Bucherer-Berg reaction from commercially available ketones.

Scheme I

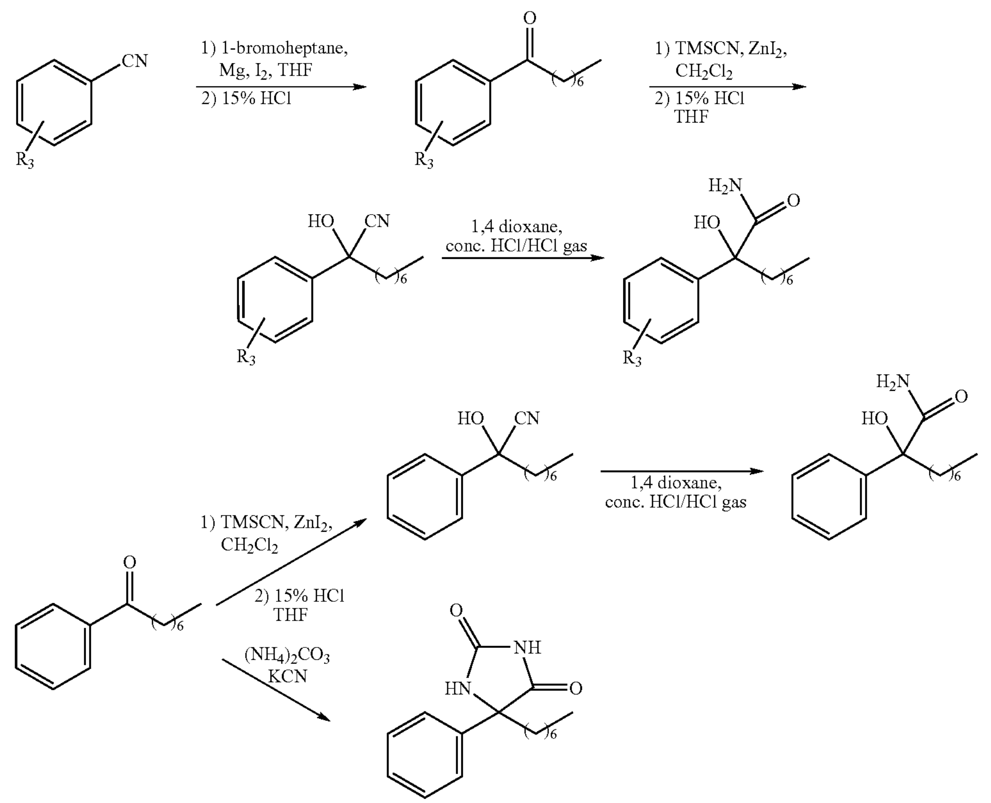

-continued

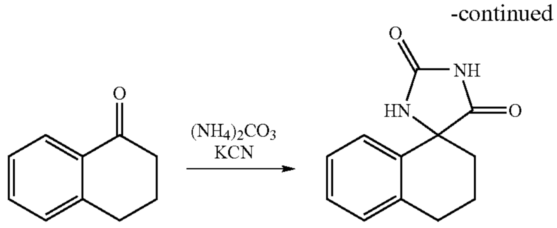

66

Enantioselective Synthesis of Hydroxyamides Using a Sharpless Dihydroxylation Strategy.

The majority of the present compounds are chiral, thus it is anticipated that scheme for preparing multi-gram amounts of each enantiomer of active analogs will be desirable. With that in mind, a general synthetic scheme (Scheme II) was prepared and S(−)-2 was successfully synthesized. Using an enantioselective Sharpless dihydroxylation strategy, the alkene 109 was converted to the diol 110 in the presence of AD mix α or β. The chiral diol 110 was oxidized to the chiral hydroxyacid 111 and converted to the chiral enantiomer with retention of stereochemistry. It is anticipate that this methodology can be adapted to synthesize any of the other enantiomers of racemic hydroxyamides proposed in this study that prove to have effectiveness against prostate cancer cell proliferation and sodium channel activity.

Scheme II

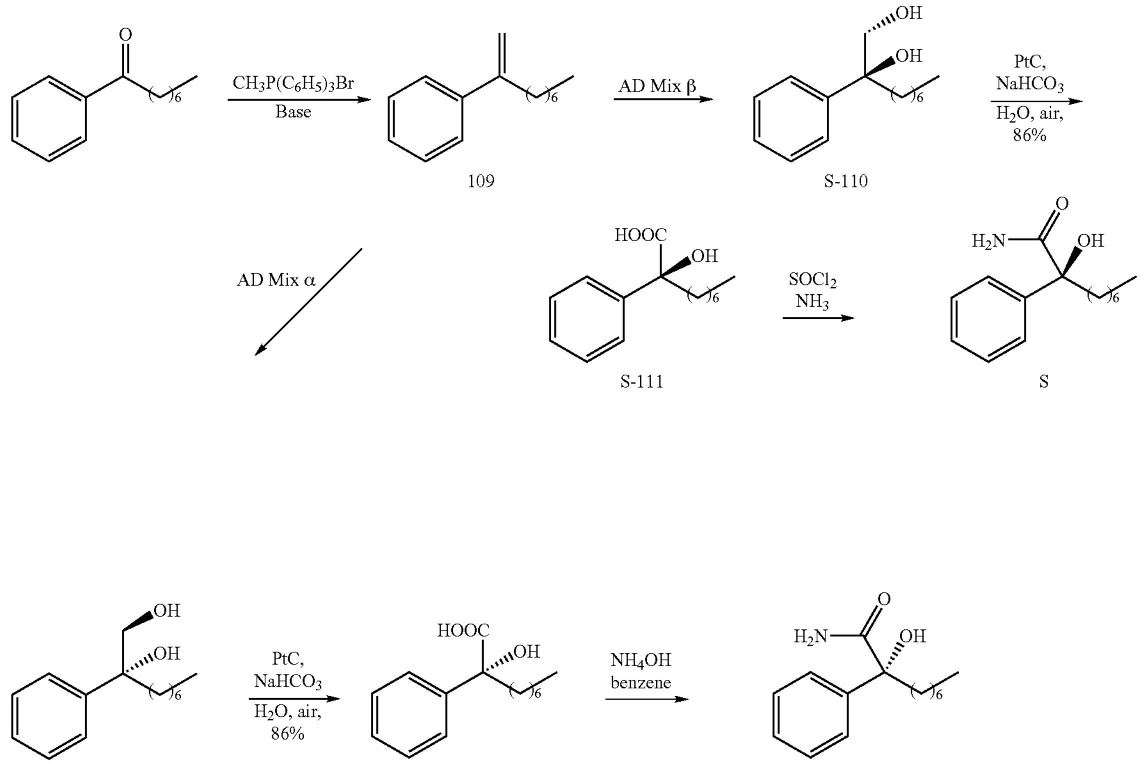

109

S-110

S-111

S

R-110

R-111

R

Enantioselective Synthesis of the Hydantoin Analogues Using a Jacobsen Catalyst Strategy.

The majority of the hydantoin compounds are also chiral, thus it is anticipated that scheme for preparing multi-gram amounts of each enantiomer of active analogs wil be desirable. With that in mind, a general synthetic scheme (Scheme III) was prepared for synthesizing R(+)-44. Jacobsen's catalyst 97 will be used to synthesize the chiral hydantoins using the imine 136 as the starting material. A synthetic route for preparing Jacobsen's catalyst and the use of that catalyst to prepare chiral hydantoin analogs is shown in Scheme III. It is anticipate that this methodology can be adapted to synthesize any of the other enantiomers of racemic hydantoins proposed in this study that prove to have effectiveness against prostate cancer cell proliferation and sodium channel activity.

Scheme III

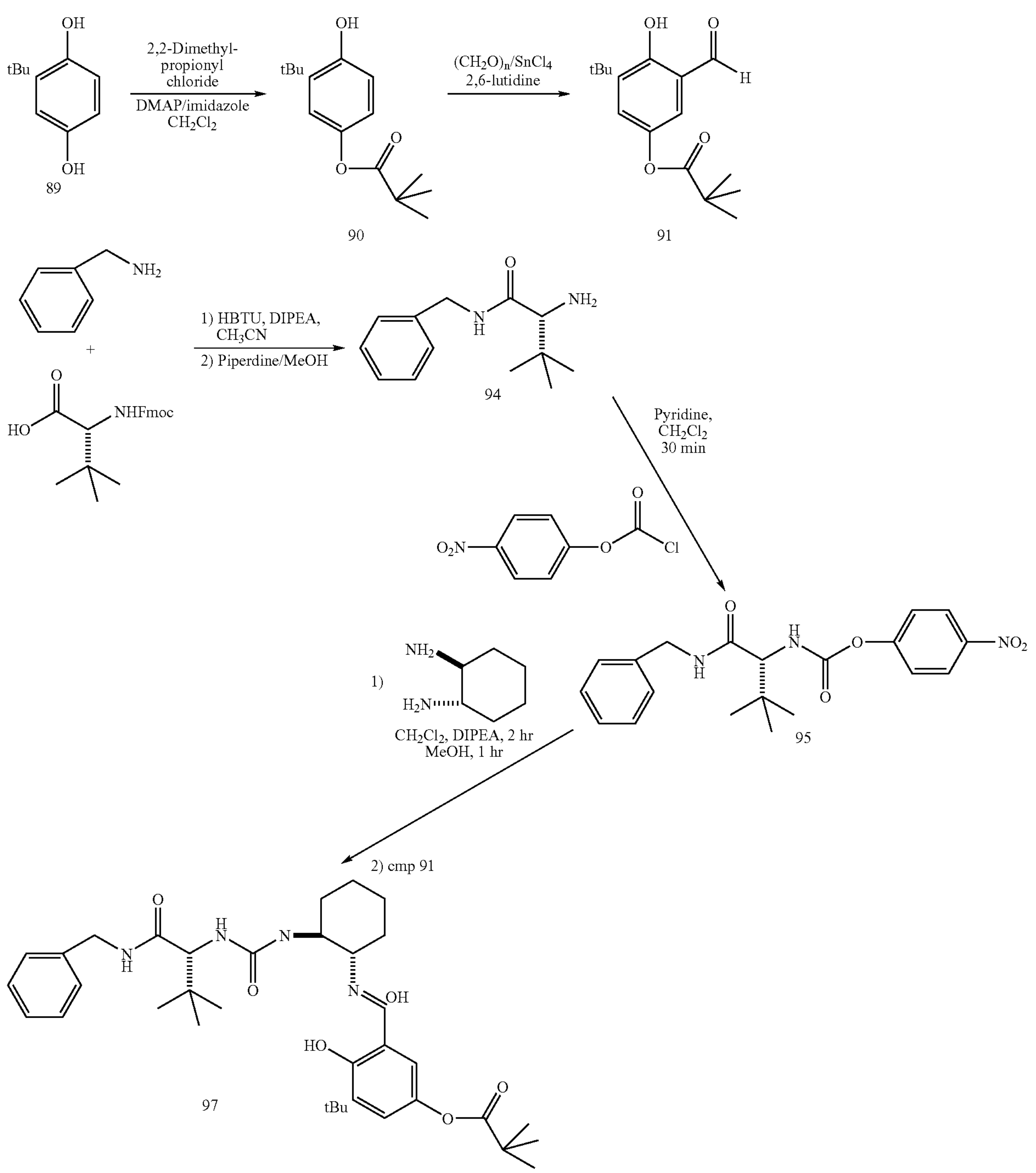

89 90 91 94 95 97

Jacobsen's catalyst 97 is then used to synthesize the chiral hydantoins (such as cmp 44). The starting material will be the imine 136:

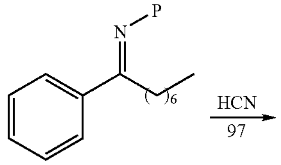

136

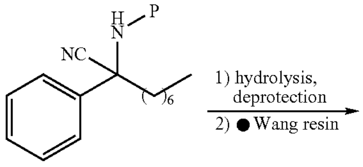

137

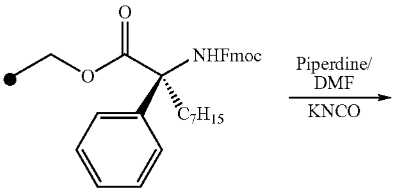

140

-continued

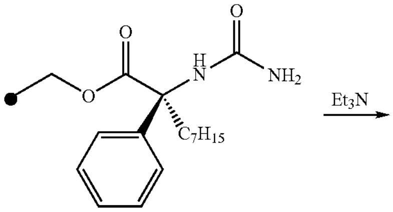

141

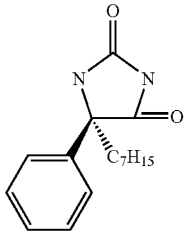

44

HCN will be added enantioselectively to the imine 136 in the presence of Jacobsen's catalyst (97) followed by hydrolysis and deprotection of 137 to give the chiral amino acid 138. Protection of the chiral amino acid 138 will generate the Fmoc protected amino acid 139. Compound 139 will be loaded onto Wang resin to give 140. Deprotection with piperidine in DMF and addition of KCNO will generate the ureide 141. Release from the resin and ring closure will be facilitated by reaction with $Et_3N$ to form (+) or (−)-44.

Additional compounds will be prepared in accordance with the following schemes:

Scheme IV

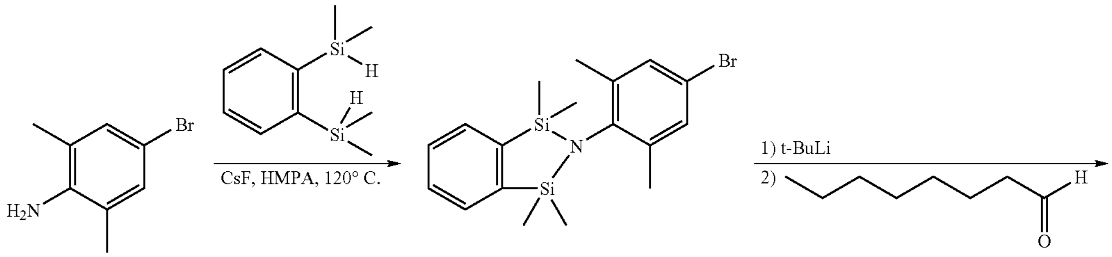

100 102

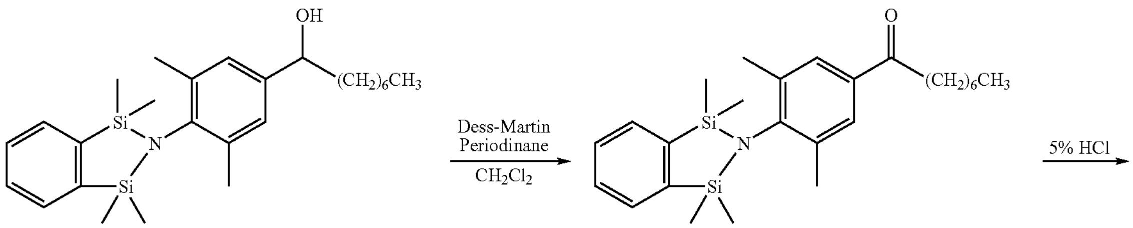

103 104

-continued
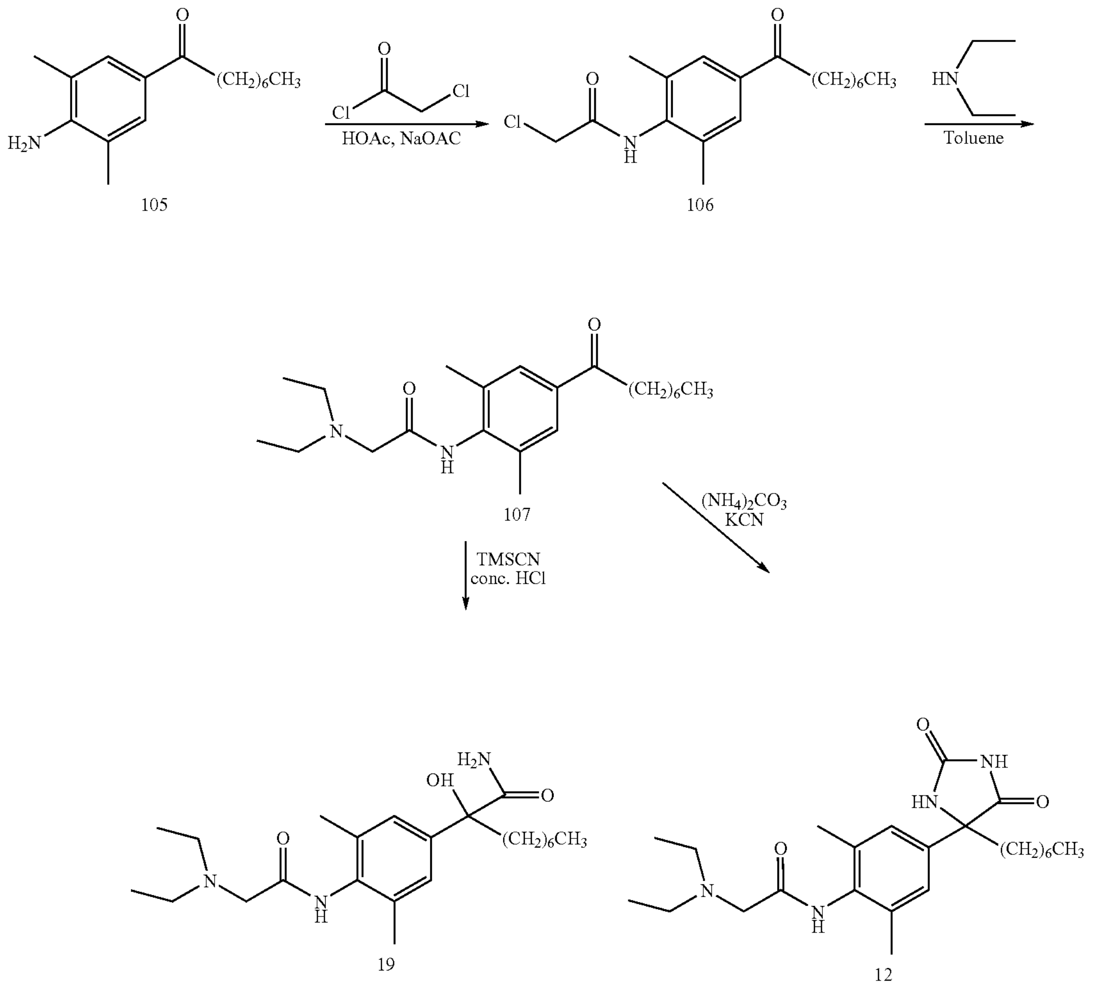
105
106
107
19
12
Scheme V
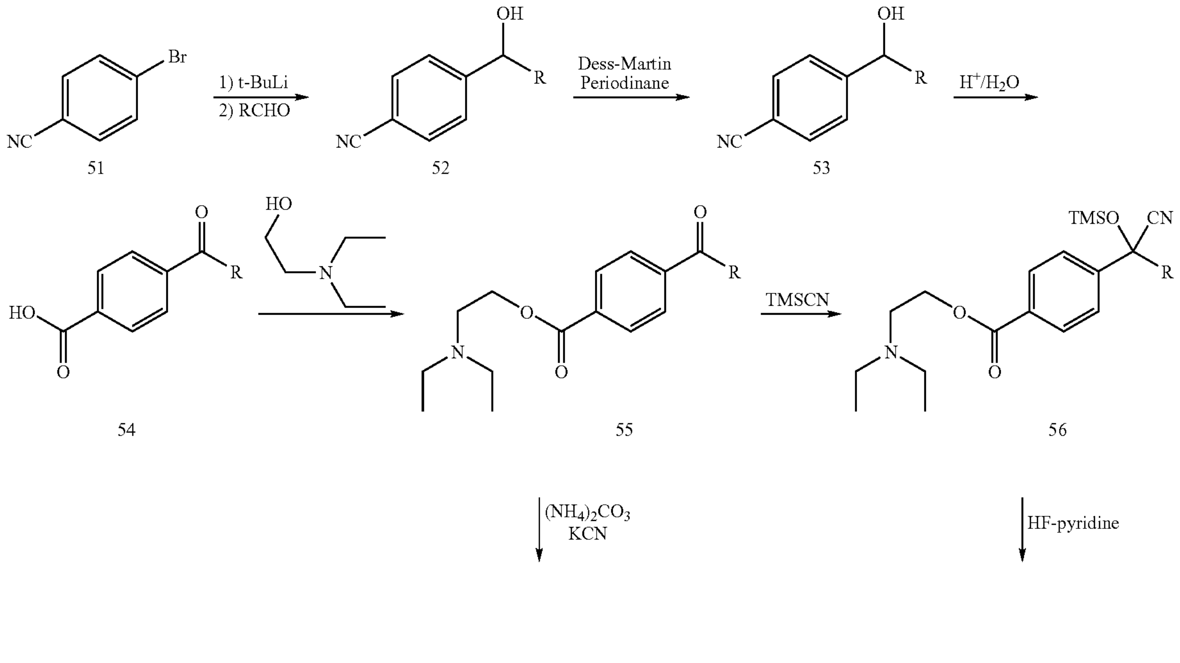
51
52
53
54
55
56

-continued
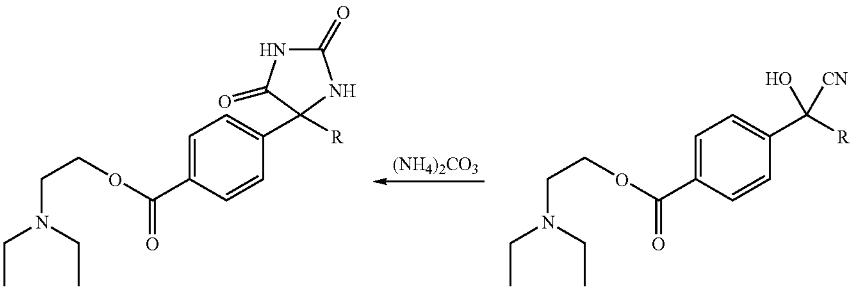
57
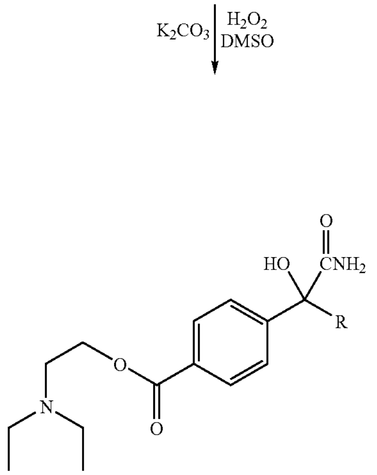
| Cmp | $R_3$ |
|---|---|
| 45 | $C_3H_7$ |
| 46 | $C_5H_{11}$ |
| 47 | $C_7H_{15}$ |
| 48 | $C_9H_{11}$ |
| 49 | $C_6H_{11}$ |
Scheme VI
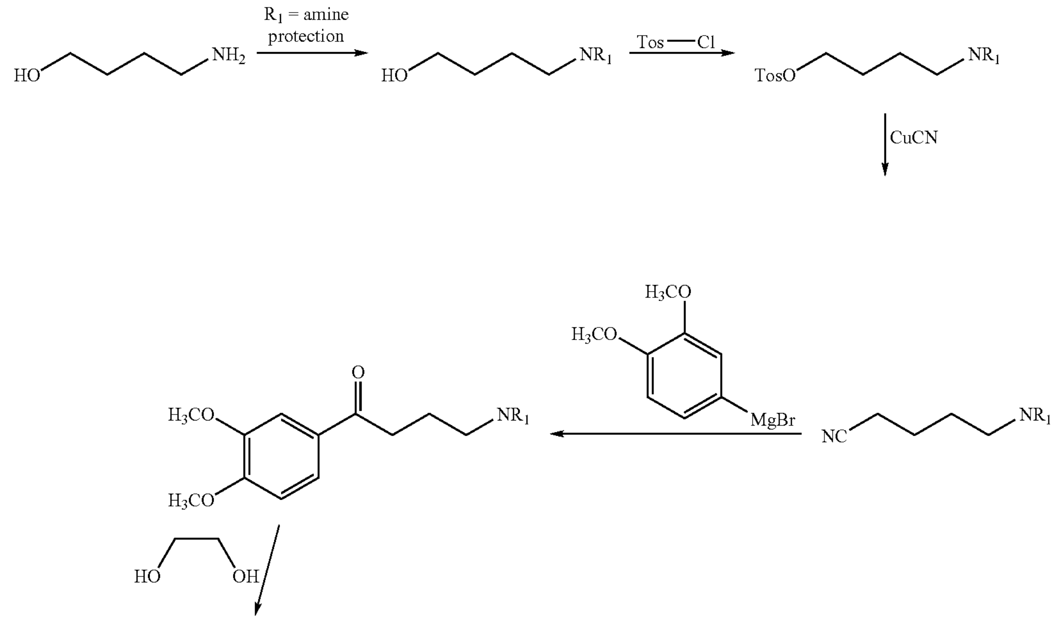

-continued
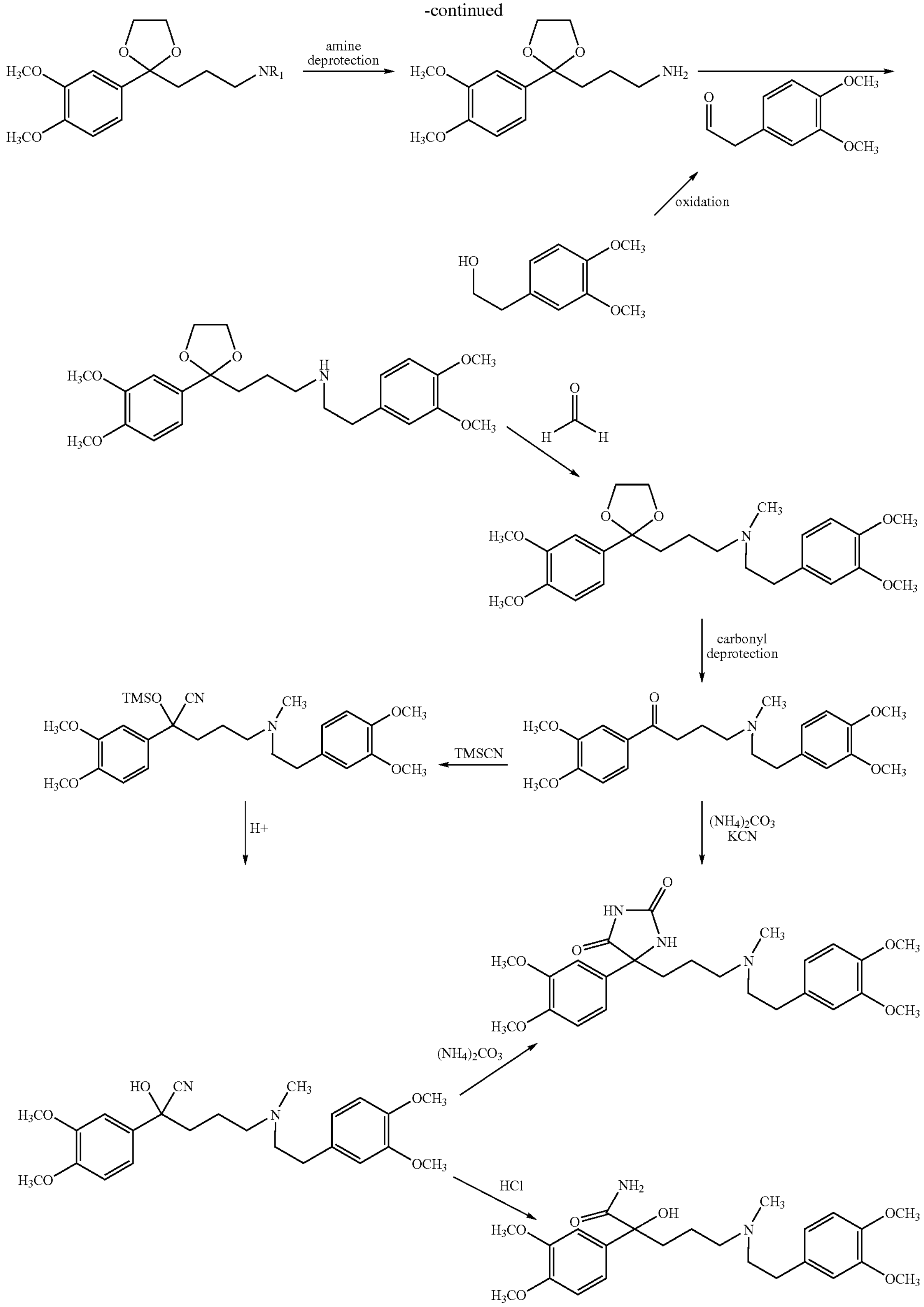

Scheme VII

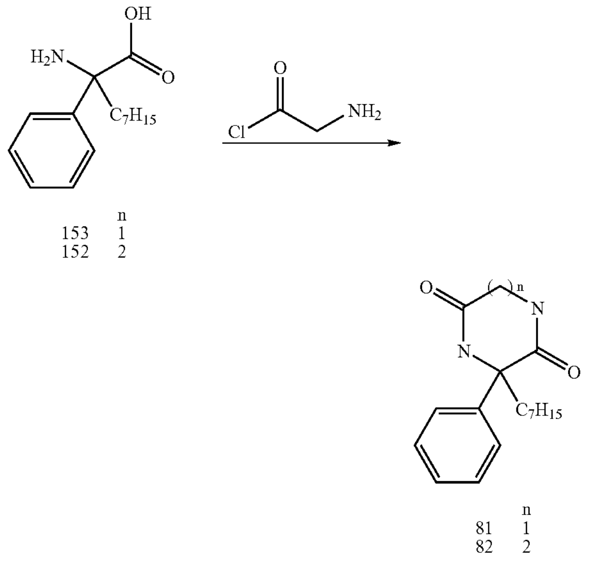

Additional compounds suitable for use in the present invention include the following:

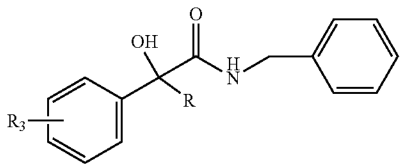

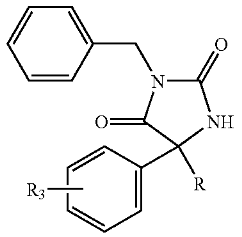

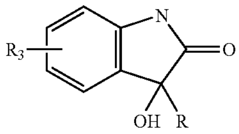

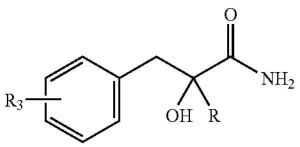

-continued

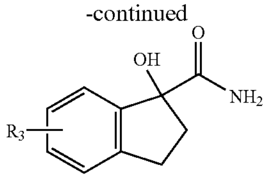

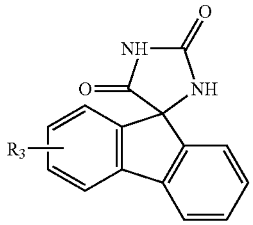

wherein $R_3$ is H or halo and R is $C_1$-$C_9$ alkyl.

EXAMPLE 2

Effects of the Synthesized Compounds on 3H-BTX-B Binding

One assay used to screen compounds for modulators of sodium channel activity, is based on the use of the radioligand 3[H]-BTX-B assay. BTX binds to site 2 on the channel protein and thus compounds that can compete with or inhibit BTX binding to the sodium channel are potential sodium channel inhibitors. This assay represents a facile tool to prescreen sodium channel binding before evaluating compounds in more rigorous functional assays such as through electrophysiology. Compound 2 and 44 demonstrate effective inhibition of 3H-BTX-B binding in comparison to phenytoin (see Table 1).

TABLE 1

3H-BTX-B Inhibition Data

| Compound | 3H-BTX-B (μM) |
|---|---|
| 5 | 9 ± 2 |
| 44 | 5 ± 1 |
| phenytoin | 40 |

| 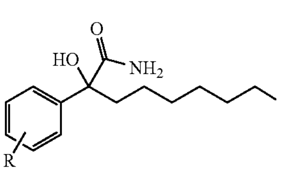 | | 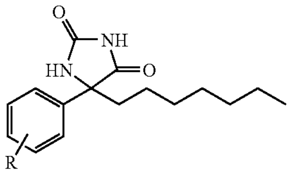 |
|---|---|---|
| NAME | R | % BTX INHIBITION (40 μM) |
| α-hydroxyamides | | |
| JDA-II-105 | H | tbd |
| JDA-xx-xxx | 2-Cl | tbd |
| JDA-III-145 | 3-Cl | 46.14 ± 2.65 |
| JDA-III-177 | 4-Cl | 48.36 ± 1.18 |

-continued

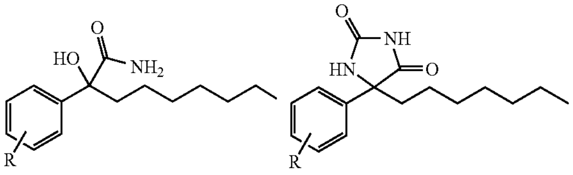

| NAME | R | % BTX INHIBITION (40 μM) |
|---|---|---|
| JDA-IV-191 | 3,4-Cl | tbd |
| JDA-IV-069 | 2-F | 37.88 ± 1.06 |
| JDA-IV-111 | 3-F | 47.96 ± 2.70 |
| JDA-xx-xxx | 4-F | tbd |
| SS-xx-xxx | 2-OMe | tbd |
| JDA-IV-067 | 3-OMe | 56.36 ± 4.33 |
| JDA-III-271 | 4-OMe | 52.55 ± 1.15 |
| JDA-xx-xxx | 2-Me | tbd |
| JDA-IV-093 | 3-Me | 43.69 ± 0.51 |
| JDA-IV-095 | 4-Me | 25.37 ± 0.06 |
| | Hydantoins | |
| JDA-I-073 | H | tbd |
| JDA-III-105 | 2-Cl | 41.61 ± 5.36 |
| JDA-III-135 | 3-Cl | 69.57 ± 3.34 |
| SS-xx-xxx | 4-Cl | tbd |
| IDA-III-113 | 3,4-Cl | 9.25 ± 3.25 |
| JDA-xx-xxx | 2-F | tbd |
| JDA-xx-xxx | 3-F | tbd |
| JDA-III-179 | 4-F | 11.71 ± 4.51 |
| JDA-II-053 | 2-OMe | 35.29 ± 0.46 |
| JDA-II-047 | 3-OMe | 37.80 ± 0.64 |
| JDA-IV-273 | 4-OMe | tbd |
| JDA-xx-xxx | 2-Me | tbd |
| JDA-xx-xxx | 3-Me | tbd |
| JDA-xx-xxx | 4-Me | tbd |

EXAMPLE 3

Electrophysiology: Effects of the Synthesized Compounds on Sodium Currents.

The functional sodium channel blocking ability of several synthetic compounds was measured using electrophysiological. Using chinese hamster ovary cells (CHO cells) stably expressing the sodium channel isoform, Nav1.5, sodium currents were elicited from a holding potential of −120 mV to a series of voltages ranging from −80 mV to +60 mV in steps of 5 mV for 25 ms. These current-voltage recordings were made in the absence and presence of drug and following washout. All effects were fully reversible on washout thus indicating that the compounds were not toxic to the cells. Table 2 lists the recorded IC50 obtained for all the compounds tested. The results of these studies demonstrate directly that the present compounds block Na channel currents.

TABLE 2

| Compound | $EC_{50}$ (μM) n = 5-7 |
|---|---|
| 1 | 14.7 ± 0.4 |
| 2 | 12.7 ± 2.7 |
| 5 | 166.4 ± 44.1 |
| 9 | 34.2 ± 7.4 |
| 44 | 29.8 ± 4.2 |
| phenytoin | >200 |

EXAMPLE 4

Effects of Sodium Channel Blockers on Androgen Dependent, and Independent Cell Lines.

The novel sodium channel blockers were assayed for activity against paired sets of cell lines with increasing metastatic potential, PC-3 and PC-3M (already androgen independent, AI), or increasing metastatic potential with increasing androgen independence, LNCaP and C4-2. DU145 was also included to provide another AI cell line with intermediate tumorigenicity between the LNCaP series and the PC-3 derivatives. This strategy allows an examination of at least three different genotypes for comparison of drug efficacy. Several biological assays have been used in the initial screening of these sodium channel analogues. The first assay used to screen these compounds was 3H-thymidine uptake in PC-3 cells. The cells were trypsinized, equal cell numbers were placed into each well and allowed to recover overnight. The medium was changed the next day and the analogues were added at the concentration indicated in Table 3. Analogue 2, and the hydantoin analogue 44, inhibited DNA synthesis better than phenytoin at all dosages tested. Indeed, at higher concentrations, phenytoin was stimulatory as was analogue 4, at all dosages tested. These data confirmed the anticipated success of the design strategy that was invoked by the receptor targeted scheme outlined above.

TABLE 3

Inhibition of PC3 Cells

| | Concentration (μM) | | | | | | |
|---|---|---|---|---|---|---|---|
| | 100 | 40 | 20 | 10 | 1 | 0 | Compound |
| %/ | 30.75 | −12.54 | −21.78 | −13.93 | −23.77 | 0 | Phenytoin |
| Inhi- | 81.99 | 55.09 | 32.70 | 26.64 | 12.75 | 0 | 44 |
| bition | −13.36 | −42.58 | −71.62 | −53.19 | −41.03 | 0 | 4 |
| | 96.20 | 48.90 | 44.58 | 25.25 | −3.61 | 0 | 2 |

To determine the novel sodium channel blockers are cytostatic or cytotoxic inhibitors, studies were performed using MTT after treating PC-3 cells with the analogues. In these assays the MTT compound is taken up by live cells in the culture and converted to insoluble formazan crystals by functional respiratoring mitochondria. These crystals can then be solubilized in DMSO or acid-EtOH and the absorbance measured at 570 nM to determine the relative number of viable cells in a culture. The results from these studies indicate that the compounds have only a marginal impact on cell viability after 24 hours of treatment. A reduction in viability is only seen at the highest dose tested, 100 μM. This dose is in great excess over the apparent IC50 of 30 μM for the inhibitory compounds.

Long-term growth assays (7 days with drug) were also initiated to determine if the effects observed were stable or transient. C4-2 cells were plated at cell densities established previously to reach saturation at day 7. The cells were allowed to recover overnight before a media change with the analogues (all at 40 μM) was performed. The assays were terminated at day 1, 3, 5 and 7. Media changes were performed on day 0, 2, 4 and 6 with fresh analogues added each time. The cells were then fixed with glutaraldehyde and stained with crystal violet. The dye is then eluted in Sorenson's solution and the absorbance read at 540 nM. The results of a representative growth assay for C4-2 cells is shown in FIG. 10. These results show a remarkable inhibition of growth by the hydroxyamide compound 1. Hydantoin analogue 5, had intermediate efficacy while a similar analogue 66, had no discernible effect from the control and may have been mildly stimulatory as was also observed for the lidocaine control. These results with the AI, human prostate cancer cell line, C4-2, were not exclusive to C4-2. These assays were repeated for DU145, PC-3 and the paired metastatic cell line PC-3M. The data were normalized to the day 7 DMSO control for each cell line to allow for direct cell:cell comparison. These data demonstrated two important points. Firstly, the hydroxyamide analogue 1 quite effectively inhibited growth of all PCa cell lines tested to date inhibiting the cells' growth to a maximum of 20-25% of controls. Secondly, the hydantoin class of analogues, 44 and 66 show cell selective inhibition of growth. The IC50 was determined for compounds 1, 2, 5 and 44 at day five for several of our channel blockers against the matched panel of PCa cell lines (Table 4). Remarkably, the data shows that compounds which demonstrated the most active sodium channel blockade (compounds 1 and 2 vs 5 and 44) were the best inhibitors of prostate cancer cell proliferation.

deprives them of a substratum with which to adhere. One hallmark of cancer cells is their ability to grow in an anchorage-independent manner. Colony formation on soft-agarose simulates the 3-D, anchorage-independent growth of a tumor. When normal cells are grown under similar conditions they rapidly apoptose. In order to determine the possible efficacy of these compounds to inhibit tumor formation, several compounds were screened using SACF. The sodium channel blockers have increased inhibitory activity in 3-D growth relative to that seen in 2-D growth assays when tested using molar equivalence to the phenytoin IC50. Compounds 1 and 2, which were the best compounds in 2-D growth assays (66.3% and 42.3% inhibition) increase to approximately 87.2% and 62% inhibition at the same concentration in 3-D growth as compared to phenytoin. It should also be emphasized that the colonies that do form are much smaller in the test compound plates as compared to phenytoin. Therefore, the reduction in colony formation is even more dramatic than indicated by the shear numbers alone. Secondly, compounds that had marginal impact on cell growth in 2-D, namely compound 2, show dramatically enhanced inhibition (41.5% of phenytoin) using SACF. These data indicate that several compounds have potential to inhibit tumor growth in vivo. Interestingly, phenytoin itself is somewhat inhibitory in these 3-D assays. Phenytoin inhibited 25.7% of SACF compared to the DMSO/EtOH control plates.

TABLE 4

Effects of Sodium Channel Blockers on Prostate Cancer Cell Proliferation (Day 5)

| | Day Five Effects on Cell line IC50 (μM) ± S.E.M. | | | | | $Na^+$ Channel Blockade $EC^{50}$ |
|---|---|---|---|---|---|---|
| Compound | C4-2 | PC3 | DU-145 | PC-3M | LNCaP | (μM) |
| 1 | 51.3 ± 0.2 | 66.0 ± 0.7 | 56.0 ± 0.7 | 61.9 ± 0.1 | 72.2 ± 0.1 | 14.7 ± 0.4 |
| 5 | 61.8 ± 0.0 | >100 | 84.3 ± 2.2 | 69.9 ± 1.3 | 81.3 ± 0.5 | 166.4 ± 44.1 |
| 2 | 61.1 ± 0.1 | 66.8 ± 1.2 | 67.2 ± 0.1 | 50.0 ± 0.0 | 64.1 ± 4.3 | 12.7 ± 2.7 |
| 44 | 67.4 ± 1.3 | 66.0 ± 0.1 | 35.6 ± 2.6 | 58.4 ± 0.0 | 71.8 ± 1.8 | 29.8 ± 4.2 |

EXAMPLE 5

Effects of Sodium Channel Blockade on PSA Secretion and Cell Migration.

PSA levels are clinically important in following tumor progression and burden. Sodium channel blockers 1, 2 and 44 (at 40 μM) and phenytoin at (100 μM) were investigated for their ability to suppress PSA secretion by PCa C4-2 cells. Compounds 1 and 2 significantly decreased PSA secretion on a per cell basis by 42.5% and 41.8%, respectively. Phenytoin was less effective at inhibiting PSA secretion (17.8% at 100 μM) and compound 44 inhibited secretion by 14.9% at 40 μM. Remarkably, this trend reflects the ability to block sodium channels and the effects on cell proliferation. Further, the dose-response curve of compound 1 for reducing PSA revealed an IC50 of approximately 10 μM, which matches the sodium channel EC50 of 14.7 μM. This raises very new and interesting questions as to the role of ion channels on PSA secretion pathways.

Soft agarose colony formation (SACF) is a technique for growing cells suspended in a 3-dimensional (3-D), semi-solid medium. Growing single cells in this manner using agarose Evaluation of Compound 1 Toxicity in Mice.

In collaboration with the NIH National Institute of Neurological Disorders and Stroke, compound 1 has been evaluated for acute toxicity in mice (Table 5). The data reveals that compound 1 is tolerated up to 300 mg/kg with ¾ animals exhibiting a short term (0.5 hrs) impairment of balance at this high dose. There were no reports of death, spasms or respiratory distress with i.p. administration of compound 1.

In summary, thymidine incorporation, MTT, crystal violet assays, PSA, soft agar colony formation and patch clamping methodologies have been used to date and provide insightful information as to the activity of the claimed compounds. Further, preliminary toxicity data obtained in mice reveal compound 1 to be tolerated up to 300 mg/kg with a half an hour impairment in balance. No acute toxic effects (death, seizures, ataxia, cardiac arrest or loss of respiratory drive) were observed. Taken together, these preliminary studies point towards two classes of compounds, hydroxyamide and hydantoin, which actively inhibit PCa cell growth.

TABLE 5

| NIH Evaluation of Compound 1 in Mice for impairment of Balance on Rotorod | | | | |
|---|---|---|---|---|
| | Time (hours) | | | |
| Dose (mg/kg)[b] | 0.25 | 0.5 | 1.0 | 4.0 |
| 30 | — | 0/4 | — | 0/2 |
| 100 | 0/4[a] | 1/8 | 1/8 | 10/4 |
| 300 | — | 3/4 | — | 0/2 |

[a]Number of mice with impaired balance on the rotating rod/total # of animals tested. No deaths, spasms or respirator distress reported.
[b]Dose administered i.p.

The invention claimed is:

1. A sodium channel blocker represented by the structure:

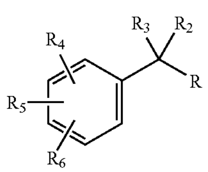

I wherein R is selected from the group consisting of $C_1$ alkyl, $C_3$-$C_6$ alky, $C_8$-$C_{12}$ alkyl, $C_2$-$C_9$ alkenyl, $C_2$-$C_9$ alkynyl, $—(CH_2)_m COOH$, $—(CH_2)_m NH_2$, $—(CH_2)_m CONH_2$, $—(CH_2)_n C_3$-$C_6$ cycloalkyl, $—(CH_2)_n$aryl, $—(CH_2)_n$ aryl, $—(CH_2)_p NCH_3(CH_2)_p$ aryl and $—(CH_2)_n$ heterocyclic, wherein m is an integer ranging from 3-8, n is an integer ranging from 0-4 and p is an integer ranging from 1-4;

$R_2$ is $—(CH_2)_n CONH_2$, wherein n is 3 or 4;

$R_3$ is hydroxyl;

$R_4$ and $R_5$ are both H; and $R_6$ is

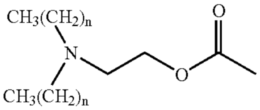

wherein n is an integer ranging from 0-2.

2. A sodium channel blocker represented by the structure:

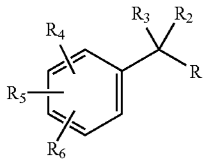

I wherein R is selected from the group consisting of $C_1$ alkyl, $C_3$-$C_6$ alky, $C_8$-$C_{12}$ alkyl, $C_2$-$C_9$ alkenyl, $C_2$-$C_9$ alkynyl, $—(CH_2)_m COOH$, $—(CH_2)_m NH_2$, $—(CH_2)_m CONH_2$, $—(CH_2)_n C_3$-$C_6$ cycloalkyl, $—(CH_2)_n$aryl, $—(CH_2)_n$ aryl, $—(CH_2)_p NCH_3(CH_2)_p$ aryl and $—(CH_2)_n$ heterocyclic, wherein m is an integer ranging from 3-8, n is an integer ranging from 0-4 and p is an integer ranging from 1-4;

wherein $R_2$ is $—(CH_2)_n CONH_2$, wherein n is 3 or 4;

$R_3$ is hydroxyl;

$R_4$ and $R_5$ are both $C_1$-$C_4$ alkyl; and $R_6$is

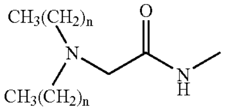

wherein n is an integer ranging from 0-2.

3. A sodium channel blocker represented by the structure:

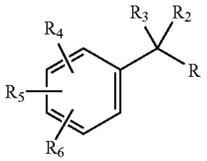

I wherein R is

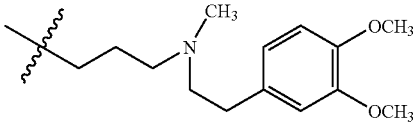

or

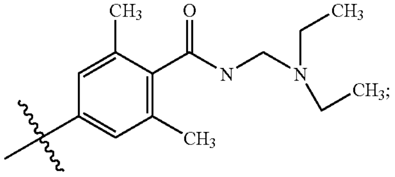

;

wherein $R_2$ is $—(CH_2)_n CONH_2$,wherein n is 3 or 4;

$R_3$ is hydroxyl;

$R_4$ and $R_5$ are independently selected from the group consisting of H, halo and $C_1$-$C_4$ alkoxy; and $R_6$ is H.

* * * * *